United States Patent [19]

Nicholas

[11] Patent Number: 5,276,222
[45] Date of Patent: Jan. 4, 1994

[54] PREPARATION OF 4,4,4-TRIFLUORO-2-METHYL-1-BUTENE BY THE DEHYDROCHLORINATION OF 3-CHLORO-1,1,1-TRIFLUORO-3-METHYL-BUTANE

[75] Inventor: Paul P. Nicholas, Broadview Heights, Ohio

[73] Assignee: The B. F. Goodrich Company, Akron, Ohio

[21] Appl. No.: 713,917

[22] Filed: Jun. 12, 1991

Related U.S. Application Data

[62] Division of Ser. No. 514,828, Apr. 26, 1990, Pat. No. 5,032,648.

[51] Int. Cl.$^5$ .............................................. C07C 21/18
[52] U.S. Cl. ..................................................... 570/136
[58] Field of Search .......................................... 570/136

[56] References Cited

U.S. PATENT DOCUMENTS

| | | | |
|---|---|---|---|
| 2,490,753 | 12/1949 | Hill et al. | 570/136 |
| 2,617,836 | 11/1952 | Pearlson et al. | 570/136 |
| 2,668,182 | 2/1954 | Miller | 570/136 |
| 2,888,447 | 5/1959 | Martin et al. | 570/136 |
| 4,902,835 | 2/1990 | Kende et al. | 570/136 |
| 5,017,718 | 5/1991 | Ojima et al. | 570/136 |
| 5,026,928 | 6/1991 | Tonelli et al. | 570/136 |

FOREIGN PATENT DOCUMENTS 1-143840  6/1989  Japan .

OTHER PUBLICATIONS

March, J. *Advanced Organic Chem* 1977 p. 935 "Dehydrohalogenation of Alkyl Halides".

*Primary Examiner*—C. Warren Ivy
*Assistant Examiner*—A. A. Owens
*Attorney, Agent, or Firm*—Nestor W. Shust

[57] ABSTRACT

The partially fluorinated alkene 4,4,4-trifluoro-2-methyl-1-butene is produced by the selective dehydrochlorination of 3-chloro-1,1,1-trifluoro-3-methylbutane in the presence of a suitable base at elevated temperatures. The alkene is converted to 1,2-epoxy-4,4,4-trifluoro-2-methylbutane which is polymerizable in the presence of an aluminum coordination catalyst. A copolymer can be made with epichlorohydrin.

8 Claims, No Drawings

PREPARATION OF 4,4,4-TRIFLUORO-2-METHYL-1-BUTENE BY THE DEHYDROCHLORINATION OF 3-CHLORO-1,1,1-TRIFLUORO-3-METHYLBUTANE

This is a division of parent application Ser. No. 07/514,828 filed on Apr. 26, 1990, now U.S. Pat. No. 5,032,648.

FIELD OF THE INVENTION

The present invention relates to a selective dehydrochlorination process for producing 4,4,4-trifluoro-2-methyl-1-butene, its epoxide, 1,2-epoxy-4,4,4-trifluoro-2-methylbutane, and the polymerization thereof, none of which has previously been known.

BACKGROUND

An article by H. C. Brown and J. I Moritanio, J. Am. Chem. Soc., Vol. 75, page 4112, 1953, relates to the ability of highly hindered alkoxide bases to direct dehydrohalogenation of 2-bromo-2-methylbutane to yield more 2-methyl-1-butene than the isomeric 2-methyl-2-butene.

SUMMARY OF THE INVENTION

The partially fluorinated alkene, 4,4,4-trifluoro-2-methyl-1-butene, is prepared by the selective dehydrochlorination of 3-chloro-1,1,1-trifluoro-3-methylbutane with basic oxide or hydroxide derivatives of Group 1A and Group 2A metals, and the like. Specific examples include $Na_2O$, NAOH, CaO, BaO and preferably MgO. To a lesser extent sterically hindered alkyl substituted aromatic amines can be used wherein the substituents are primary, secondary, or tertiary alkyl groups having from 1 to 7 carbon atoms, and preferably 1 to 4 carbon atoms, especially 2-monosubstituted or 2,6-disubstituted pyridines, e.g. 2-tert-butylpyridine, 2,6-lutidine, and the like. The dehydrochlorination process is conducted at about 100° C. to about 300° C. and preferably at about 150° C. to about 250° C. The epoxide derivative, 1,2-epoxy-4,4,4-trifluoro-2-methylburane, can be homopolymerized to form an oligmer or copolymerized with a monomer such as epichlorohydrin using an aluminum coordination catalyst.

DETAILED DESCRIPTION OF THE INVENTION

A two-step process can be utilized to produce the precursor, 3-chloro-1,1,1-trifluoro-3-methylbutane (1).

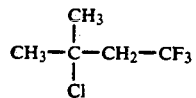

(1)

In the first isobutylene is reacted with carbon tetrachloride in the presence of a radical initiator, benzoyl peroxide, resulting in 2,4,4,4-tetrachloro-2-methylbutane. The procedure is similar to that described in M. S. Kharasch, E. V. Jensen and W. H. Urry, J. Am. Chem. Soc. Vol. 69, 100 , 1947, W. A. Nugent and Jay K. Kochi, J. Oranomet. Chem., Vol. 124, 327, 1977. In the second step, 2,4,4,4-tetrachloro-2-methyl-butane is contacted with liquid hydrogen fluoride to produce 3-chloro-1,1,1-trifluoro-3-methylbutane (1). This procedure is similar to that reported in P. Tarrant, J. Attaway, and A. M. Lovelace in J. Am. Chem. Soc., Vol. 76, 2343, 1954.

The precursor (1) is selectively dehydrochlorinated to essentially produce the fluoroalkene, 4,4,4-trifluoro-2-methyl-1-butene (2)

(2)

which contains a terminal double bond. The selectively of this step is generally attributed to the stearic features of the bases, the reaction temperature, and the critical presence of the trifluoromethyl group in (1). Two types of bases demonstrate the requisite selectivity for the partially fluorinated alkene (2) of the present invention. The first type is the oxide and hydroxide derivatives of Group 1A and preferably the Group 2A metals. Examples include BaO, CaO, $Na_2O$, NAOH, KOH, and the like, with MgO being preferred. The second type is sterically hindered aromatic amines, such as alkyl substituted pyridines. These are less desirable inasmuch as the requisite selectivity is lower. Generally, the alkyl substituent can be located at any position of the pyridine ring but preferably at either the 2-position or the 2,6-positions of the pyridine ring where stearic hindrance is most strongly expressed. The alkyl substituents can be primary, secondary, or tertiary alkyl groups having from about 1 to about 7 carbon atoms, preferably from about 1 to about 4 carbon atoms, with specific examples including 2-tert-butyl pyridine, 2,6-lutidine, and the like.

The substituted pyridines used in the dehydrochlorination reaction can generally be dissolved in a hydrocarbon solvent or used neat whereas the metal oxides are suspended as powders in a hydrocarbon solvent. Suitable solvents include alkanes containing from about 6 to about 10 carbon atoms, for example nonane.

The dehydrochlorination process is conducted by heating the precursor (1) and the base to an elevated temperature. The selectivity for the 1-alkene of the present invention over the isomeric 2-alkene, 1,1,1-trifluoro-3-methyl-2-butene (3), increases with increasing reaction temperature. Suitable reaction temperatures are from about 100° C. to about 300° C. and preferably from about 150° C. to about 250° C. Generally some 1,1,1-trifluoro-3-methylbutane (4) is also produced when alkyl substituted pyridines are used. However, very little of the fluorobutane (4) forms when MgO powder and CaO powder are used under the proper conditions. Selectivities for the 1-butene (2) on the order of 30 to 50 percent are readily obtained, desirable amounts of at least 85 percent, and preferably at least 95 percent and even 99 percent are favored. Ratios of the 1-butene to 2-butene on the order of at least 500 are readily produced when the preferred metal oxide, i.e., MgO, is used at the preferred temperatures. Generally, the amount of base can vary greatly depending upon how it is used. Amines, for example, are generally used as both solvent and reactant. With metal oxides, the amount can vary from near stoichiometric amounts to exceedingly large excesses, as in a fluid bed reactor.

The alkene 4,4,4-trifluoro-2-methyl-1-butene (2) can be used as a refrigerant or as a component in any amount with other refrigerants such as the various chlorofluorohydrocarbons. It is also useful as an intermediate in the synthesis of the corresponding partially fluorinated epoxide monomer. The present invention will be better understood by reference to the following examples.

EXAMPLE 1

Preparation of 2,4,4,4-Tetrachloro-2-methylbutane

A 2960 mL autoclave was charged with 210.8 g (3.75 mol) of isobutylene, 1153.5 g (7.50 mol) of carbon tetrachloride, and 56.9 g of benzoyl peroxide. The mixture was shaken, heated to 100° C., and held there for four hours. Maximum pressure reached was approximately 90 psig. The dark reaction product was filtered and combined with the crude product from a second run. The combined products were distilled through an 8 inch vacuum-jacketed column packed with glass rings, bp 61°-2° C./10 mm, 451.7 g.

EXAMPLE 2

Preparation of 3-Chloro-1,1,1-trifluoro-3-methylbutane (1)

A 2960 mL autoclave was charged with 776 g (3.68 mol) of the tetrachloride from Example 1 and sealed. A shut-off valve with a ¼ in male Swagelok fitting was attached to the head along with a Monel pressure gauge. The autoclave was cooled in an ice bath and a 20 mm vacuum applied. Liquid hydrogen fluoride was then charged through the shut-off valve from an inverted lecture bottle and a line of Teflon tubing. Flow was controlled with a stainless steel needle valve. The reactor was then heated to 60° C. with shaking and maintained there for 2.5 hours, during which time the pressure increased to 705 psig. The autoclave was then cooled in ice, vented, then pressurized and vented several times with nitrogen. It was then opened and 120 mL of pyridine added. The contents were then recovered and combined with a 150 mL octane rinse. The crude product was distilled through a short Vigreaux column and the distillate collected up to a pot temperature of 142° C. Distillation was stopped at this point due to the accumulation of a white solid in the condenser. A total of 333.4 g of clear, colorless liquid was collected. This was washed with water, dried and redistilled through a spinning band column, bp 69° C., 273.8 g (>99.7 percent pure).

EXAMPLE 3

Dehydrochlorination of 3-Chloro-1,1,1-trifluoro-3-methylbutane (1) With the Potassium Salt of 3-Ethyl-3-pentanol A 3-neck, 25 mL flask was fitted with a condenser and gas bubbler, septum, argon inlet, thermometer, and a magnetic stirring bar. The flask was charged with 0.28 g (7.18 mmol) of potassium metal and 15 mL of 3-ethyl-3-pentanol under argon. The mixture was stirred at 30° C. until all the potassium had been consumed, and 1.51 g (9.41 mmol) of precursor (1) was injected. A rapid exotherm to 40° C. occurred as the solution became turbid with the precipitation of KCl. Stirring was continued for 1.5 hours from the time the chloride was injected. Argon flow was stopped, and 200 microliters of benzene (0.1817 g) was injected. This served as the internal standard for quantitative GC analysis. Gas chromatography was performed using a 60 meter Volcol glass capillary column (0.75 mm Supelco) operating at 10° C., followed by a temperature program to 170° C. at 30° C./min. The reaction mixture analyzed for 5.40 mmol of 1,1,1-trifluoro-3-methyl-2-butene (3), 0.0173 mmol of the isomer, 4,4,4-trifluoro-2-methyl-1-butene (2), and 3.06 mmol of unreacted precursor (1) for a material balance of 90 percent, and ratio of 2-butene/1-butene=312. The dehydrochlorination product was recovered by distillation and further confirmed to be 4,4,4-trifluoro-2-methyl-2-butene by H-NMR, δ5.45 (broad s, 6) and δ1.90 (q,1,J=8 Hz), mass spect (electron impact), m/e 124.

EXAMPLE 4

Dehydrochlorination of 3-Chloro-1,1,1-trifluoro-3-methylbutane With Substituted Pyridines A 20 mL stainless steel pressure reactor was fitted with a thermowell, pressure relief valve, gauge, and a shut-off valve fitted with a rubber septum for removing liquid samples. The contents were stirred by a magnetic stirring disc. A solution was prepared comprising 10 mL of the amine, 1.50 g (9.38 mmol) of the precursor (1), and 200 microliters of benzene (internal reference), the actual delivered weight being determined following injection. This solution was then charged into the reactor and the reactor sealed. Where nonane was used as the solvent, the amine was used in 14 percent excess over the precursor (1) together with 8.75 mL of nonane. The reactor was then heated to the reaction temperature using a custom made mantle and a proportioning controller operating from the thermocouple in the reactor. Periodically, the reactor was cooled in ice, and the reactor head heated with a hot air gun to vaporize any volatiles in the lines and condense them in the reactor. Approximately 0.25 mL samples were removed for GC quantitation and the reactor reheated to the reaction temperature. The time required to heat the reaction mixture to 250° C. was about 45 min., a short interval compared to the reaction rate, particularly since the reaction is very slow below 150° C. The GC had been calibrated for the products shown in Table I using benzene as the internal standard with excellent reproducibility. The structure assignment for 1,1,1-trifluoro-3-methylbutane (4) is based on the NMR spectrum of a spinning band distillation fraction bp 40° C., containing 73 mol percent 4,4,4-trifluoro-2-methyl-1-butene (2) and 20 mole percent 1,1,1-trifluoro-3-methylbutane (4) recovered from a preparative scale experiment. This spectrum included an unaccounted for resonance at δ1.00, (d,J=6 Hz) that was present in an amount corresponding to that of the unknown component determined by GC. The C-13 NMR showed the corresponding $CF_3$ resonance slightly displaced from that of 4,4,4-trifluoro-2-methyl-1-butene.

EXAMPLE 5

Dehydrochlorination of 3-Chloro-1,1,1-trifluoro-3-methylbutane With MgO and CaO

Analytical Scale

These experiments were performed exactly as those described for the substituted pyridines of Example 4 except 10 mL of nonane was used as the solvent with 24 mmol of either MgO or CaO powder.

Preparative Scale

A 500 mL Autoclave Engineers Zipperclave pressure reactor was charged with 80 g (0.500 mol) of the precursor (1) in 230 mL of octane and 62.7 g (1.56 mol) of MgO powder. The reactor was stirred at 1000 rpm and heated to 180° C. for 10 hours. The reactor was then cooled and the following product recovery assembly attached to the shut-off valve on the reactor head. A short length of heated, flexible stainless steel tubing was connected to a 24/40 joint attached to a 100 mL, 3-neck flask fitted with a condenser. The flask was cooled in an ice bath. The shut-off valve was opened, and the stirred reactor heated as the crude 4,4,4-trifluoro-2-methyl-1-butene (2) was distilled into the flask. Heating was continued until the temperature of the reactor contents reached 120° C. This synthesis was performed three times and the products combined, giving 143 g of clear, colorless liquid. This was redistilled on a spinning band column, bp 37° C., giving 81.2 g of material >95 percent purity. This includes a 35.6 g fraction >99.6 percent. The 4,4,4-trifluoro-2-methyl-1-butene (2) has a very high vapor pressure and is easily lost. Care must be taken to keep it cold and in closed containers. H-NMR, δ1.85 (s,3), δ2.80 (q,2,J=11 Hz), δ5.01 (s,1), δ5.12 (s,1), mass spect (electron impact) m/e 124.

The results of the selective dehydrochlorination of 3-chloro-1,1,1-trifluoro-3-methylbutane with the various above bases are set forth in Table I.

TABLE I

Dehydrochlorination of 3-Chloro-1,1,1-trifluoro-3-methylbutane with Various Bases

| Base | T (°C.) | % Yield* (2) | (3) | (4) | (2) + (3) | Material Bal (%) | Conversion (%) |
|---|---|---|---|---|---|---|---|
| KOC(C$_2$H$_5$)$_3$ | 30 | 0.32 | 100 | | 0.0032 | 90 | 64 |
| 2,6-lutidine | 150 | 28 | 63 | 8.8 | 0.44 | 97 | 21 |
| | 200 | 46 | 31 | 23 | 1.5 | 98 | 96 |
| | 250 | 53 | 22 | 24 | 2.4 | 104 | 100 |
| 2,6-lutidine/ | 200 | 59 | 36 | 4.8 | 1.7 | 102 | 87 |
| nonane | 250 | 76 | 19 | 4.5 | 4.0 | 93 | 65 |
| 2-tert-butyl pyridine | 250 | 75 | 19 | 6.4 | 4.0 | 92 | 98 |
| 3,4-lutidine | 250 | 28 | 58 | 13 | 0.48 | 100 | 100 |
| MgO Powder | 150 | 85 | 15 | 0 | 5.7 | 108 | 57 |
| | 250 | 100 | 0.19 | 0.2 | 512 | 85 | 99 |
| CaO Powder | 150 | 84 | 16 | 0 | 5.3 | 103 | 37 |

(2) 4,4,4-trifluoro-2-methyl-1-butene
(3) 4,4,4-trifluoro-2-methyl-2-butene
(4) 4,4,4-trifluoro-2-methyl-butane
*Yields based on [moles of product obtained ÷ Moles of (1) converted]100

The ability of hindered potassium alkoxide bases to direct dehydrohalogenation toward terminal versus internal double bonds was originally reported by H. C. Brown. He showed that the dehydrobromination of 2-bromo-2-methylbutane could produce as much as 89 percent of the corresponding 1-butene when the base was derived from the highly hindered alcohol, 2-ethyl-1-pentanol. Table I illustrates the selectivity of various bases at different temperatures in obtaining the desired 4,4,4-trifluoro-2-methyl-1-butene (2) over the corresponding 1,1,1-trifluoro-3-methyl-2-butene (3) isomer. Following Brown's teaching, dehydrochlorination with a hindered potassium alcoholate such as potassium 3-ethyl-3-pentanolate, results in essentially 100 percent of the undesired isomer. The highest selectivity for 4,4,4-trifluoro-2-methyl-1-butene (2) is obtained with magnesium oxide suspended in nonane, which results in a remarkably high 1-butene/2-butene ratio of 512 at 250° C.

As apparent from Table I, the ratio of the terminal alkene (2) of the present invention to the internal alkene (3) obtained with potassium 3-ethyl-3-pentanolate (i.e., the base used by Brown et. al.) was extremely low. Utilization of the various pyridines generally yields alkene/alkane ratios ranging from about 1 to about 4. However, metal oxides generally gave ratios of 5 to 7 with the preferred base, magnesium oxide at the preferred temperature of 250° C., giving a ratio in excess of 500.

The presence of the trifluoromethyl group is critically important in order to achieve this high selectivity, since selectivity is lost with the unfluorinated analogue, 2-chloro-2-methylbutane. In this case, the 1-butene is the minor product, and its ratio to the 2-butene is independent of either the base or temperature.

4,4,4-Trifluoro-2-methyl-1-butene (2) is useful as an intermediate for production of the monomer, 1,2-epoxy-4,4,4-trifluoro-2-methylbutane (5)

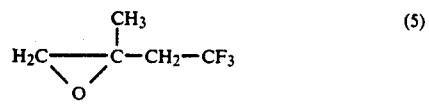

which can be polymerized by ring-opening polymerization. The epoxide (5) can be prepared in a conventional manner, for example, by treating the 1-butene (2) with 3-chloroperbenzoic acid or peracetic acid in methylene chloride.

When polymerized, the epoxide (5) gives poly(1,2-epoxy-4,4,4-trifluoro-2-methylbutane) having the repeat unit (6) containing a stable trifluoromethyl group for enhanced oil swell resistance. Moreover, the absence of either allylic or tertiary hydrogen atoms are desirable for good thermooxidative stability.

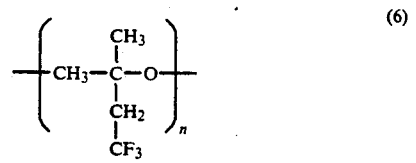

The integer n in structure (6) is a number such that the homopolymer has a weight average molecular weight of about 1,000 to 7,000. It can be prepared by treating the epoxide (5) with coordination catalysts at temperatures, from about −20° C. to about 50° C. Generally, partially hydrolyzed trialkylaluminum compounds can be used as catalysts. An example of specific suitable aluminum coordination catalysts is bis(diisobutylaluminum)oxide which is commercially available as "DIBAL-O," 25 percent solution in heptane, from Akzo Chemicals. Suitable coordination catalysts of the present invention are well known to the art. The homopolymer (6) is useful as a synthetic lubricant.

The epoxide monomer (5) can also be copolymerized with an epoxide comonomer such as epichlorohydrin (ECH) to yield polymers which can be utilized as sealants, and as gaskets when crosslinked. These polymers typically comprise mixtures of copolymer together with poly (ECH), where the overall composition is approximately 15 to 35 percent weight of (5), prepared in hydrocarbon solvents, at temperatures of $-20°$ C. to $40°$ C. They can be crosslinked with cure systems commonly used for poly(ECH).

The invention will be better understood by reference to the following examples:

EXAMPLE 6

Preparation of 1,2-Epoxy-4,4,4-trifluoro-2-methylbutane (5)

A 1 L, 3-neck flask was fitted with a thermometer, condenser, and a magnetic stirring bar, and charged with 380 mL of methylene chloride and 90 g (0.418 mol) of meta-chloroperbenzoic acid. The stirred mixture was cooled in an ice bath and 46.6 g (0.376 mol) of the 4,4,4-trifluoro-2-methyl-1-butene (2) added. The ice bath was then replaced by a water bath at room temperature. A maximum temperature of about $27°$ C. was reached. The disappearance of 4,4,4-trifluoro-2-methyl-1-butene (2) and formation of 1,2-epoxy-4,4,4-trifluoro-2-methylbutane (5) maximizes in about 6.2 hours at 83 percent conversion of 4,4,4-trifluoro-2-methyl-1-butene (2), then begins to slowly decline. The reaction was terminated after 8 hours by adding 35 mL of 10 percent sodium sulfite.

The contents are then cooled in a dry ice/acetone bath to freeze the water and cause organic acids to separate. The mixture is then filtered through a Buchner funnel, keeping the flask cooled in dry ice/acetone. The filtered solids are washed with methylene chloride cooled to $-79°$ C., and the resulting filtrate is distilled on a spinning band column. The epoxide is collected at $85°$ C., 21.54 g of 99.9 percent purity, with a forerun, bp $79°$-$85°$ C., 12.88 g, 95 percent purity. Combined yield of 1,2-epoxy-4,4,4-trifluoro-2-methylbutane (5) is 33.8 g, 0.24 mol, 64 percent. Redistillation of the forerun gives 5.36 g of 99.7 plus percent pure 1,2-epoxy-4,4,4-trifluoro-2-methylbutane (5).

EXAMPLE 7

Polymerization of 1,2-Epoxy-4,4,4-trifluoro-2-methylbutane (5) Catalyzed by DIBAL-O Heavy wall glass polymerization tubes were capped with extracted Buna N gaskets, flame dried under a flow of argon, and slightly pressurized. Solvent and monomer were charged with syringes. Distilled (5) (99.9 percent) and ECH were further dried just before use as follows: A glass tube, sealed at one end was charged with an amount of 3A molecular sieves corresponding to 25 percent of the monomer to be charged. The tube was then capped with a septum and the sieves flame dried under a flow of nitrogen. After cooling, 20-25 percent excess monomer was charged (allow for losses on hold-up) and allowed to stand for about 1 hr. with frequent shaking. The dried monomer was then removed with a syringe. The needle was then removed and replaced with a needle mounted on a vacuum-dried $0.2\mu$ Anotop 10 syringe filter (Alltech) and the appropriate volume delivered into the polymerization tube. The purpose of the filter is to remove any suspended sieve particles, but the amount present by optical inspection is small, and the filtration step is likely unnecessary. Heptane was reagent grade material used without further purification, and toluene was dried by distillation from sodium under argon. The polymerization tubes containing solvent and monomer were first equilibrated by tumbling in a constant temperature bath, then catalyst was injected. The catalyst used is DIBAL-O (25 percent in heptane) obtained from Texas Alkyls (now Akzo Chemical).

In the experiments described in Table II, 14.3 mmol of monomer was used together with 5.1 mL of solvent and 0.13 mL (0.15 mmol) of DIBAL-O. A second identical charge of catalyst was delivered after 21 hrs., with a total polymerization time of 43 hrs. The contents were transferred into tarred evaporating dishes with THF or methylene chloride rinses, as, needed. These were evaporated to dryness then vacuum-dried overnight. Aluminum-containing catalyst residues were removed by washing with a solution comprising 2 mL of concentrated aq HCl in 25 mL of methanol for 3 hrs. The methanol/HCl solution was decanted off, and the polymer rinsed with additional methanol. Both the polymer and extracts were evaporated to dryness and vacuum-dried. The residues from the extract were further extracted with THF to remove oligomers from aluminum salts. Two fractions were obtained with (5), as noted in Table II. Poly (ECH) contained only a trace of oligomer extracted by methanol/HCl. Untreated polymers of (5) contain gel and are not completely soluble in chloroform. The experiments described under runs 2 and 4 were similar except that only a single charge of catalyst was used, and run 5 was performed with a double charge of catalyst injected at time zero.

EXAMPLE 8

Copolymerization of ECH and (5)

A 7 oz. polymerization bottle was dried in a vacuum oven at $120°$ C. for 30 min., capped with an extracted Buna N gasket, then cooled to room temperature with a nitrogen purge. Toluene was dried over 3A molecular sieves in the usual way and 70 mL was injected into the capped bottle. This was followed by 9.20 g (0.0995 mol) of ECH and 12.99 g (0.0928 mol) of the fluoroepoxide (5), which were also sieve-dried. The bottle was placed in a constant temperature shaker bath and the temperature lowered to $-10°$ C. After equilibration, 4.8 mL of a 24.8 percent solution of DIBAL-O in heptane was injected (5.45 mmol). White polymer precipitated during the first 24 hr. with little further apparent change during the 69 hr. total time in the bath. The contents were transferred into an evaporating dish with 60 mL of methanol and evaporated to dryness. It was then vacuum-dried, giving 8.36 g of crude polymer containing catalyst residues. It was then placed in a 500 mL jar containing a magnetic stirring bar along with a solution comprising 350 mL of methanol and 28 mL of concentrated HCl and stirred for 3 hr. at room temperature. The insoluble rubber was then stirred overnight with a solution of 3.5 g of NAHCO$_3$ in 350 mL of water, then vacuum-dried at room temperature, giving 2.97 g of rubber designated C. The methanol/HCl extract was evaporated to dryness, giving 3.98 g of a clear, colorless oil mixed with a white, crystalline solid, the mixture designated A. This mixture was extracted with THF to separate the polymer from inorganic salts. The extract was evaporated to dryness, leaving 2.69 g of a viscous, pale yellow oil, designated B. The white THF insoluble solid (1.03 g) comprised water soluble salts.

Fraction C (2.36 g) was further separated into an acetone soluble rubber D [atactic poly(ECH)] and acetone insoluble plastic E [isotactic poly(ECH)] by stirring it with 90 mL of acetone at room temperature. The insoluble fraction was washed with an additional 10 mL of acetone and the acetone extracts combined. After vacuum-drying, fraction E comprised 0.768 g. A 15 percent aliquot of the acetone soluble fraction D was evaporated and vacuum-dried, the rest being used in the final separation by fractional precipitation with methanol.

Methanol (75 ml) was added dropwise to the stirred acetone solution of D. Turbidity developed, and the mixture was centrifuged to recover the first precipitated rubber fraction F from the clear acetone solution (0.212 g). An additional 125 mL of methanol was then added to the clear solution, and a second rubber fraction G was isolated (0.158 g). Evaporation of the clear solution and vacuum-drying recovered the remaining polymer, a viscous oil (0.870 g) designated H. The characterization of these fractions was performed by H-NMR and GPC and is described in Table III.

The following is a schematic for the Example 8 fractionation.

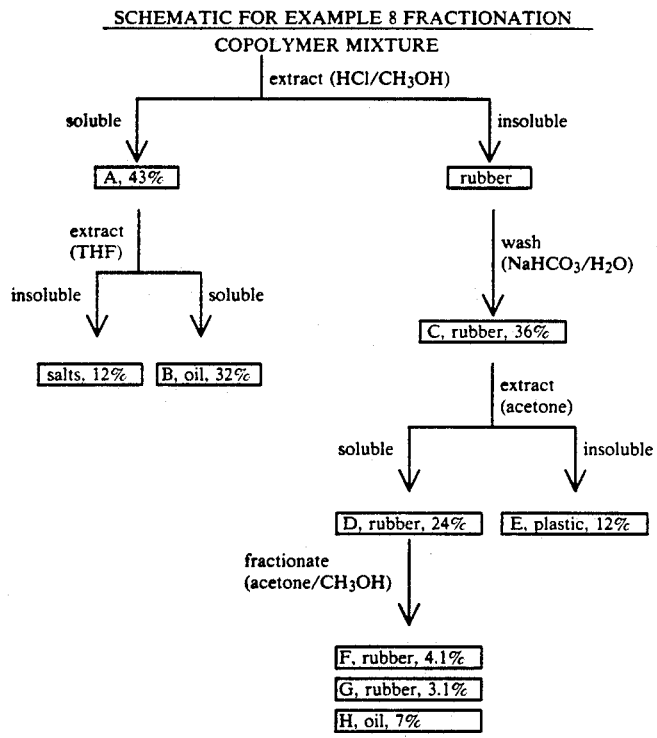

SCHEMATIC FOR EXAMPLE 8 FRACTIONATION

TABLE II

POLYMERIZATIONS CATALYZED BY DIBAL-O

| Run | Monomer | Solvent | T(°C.) | % | GPC × $10^{-3}$ (Polystyrene Equivalent) | | |
|---|---|---|---|---|---|---|---|
| | | | | | Mw | Mn | Peak |
| 1 | ECH | Heptane | 5 | 66 | 42 | 4.3 | 33 |
| 2 | ECH | Toluene | −10 | 20 | 552 | a | 1059 |
| 3 | ECH | Toluene | 5 | 39 | 158 | a | 556 |
| 4 | ECH | Toluene | 40 | 31 | 78 | a | 169 |
| 5 | (5) | Heptane | 5 | 44 | 4.4[b] | 3.3 | 4.4 |
| 6 | (6) | Toluene | −10 | 21 | 2.1[c] | 1.6 | 1.4 |
| | | | | | 3.7 | 1.4 | 3.6 |

[a] polymodal distribution
[b] HCl/methanol insol fraction (66%)
[c] HCl/methanol soluble fraction (34%)

TABLE III

CHARACTERIZATION OF FRACTIONS FROM COPOLYMERIZATION OF (5) WITH ECH

| Fraction | Composition | Mol % 5 (wt %) | GPC × $10^{-3}$ (Polystyrene Equivalent) | | |
|---|---|---|---|---|---|
| | | | Mw | Mn | Peak |
| B | Copolymer | 25 (34) | 1.4 | 0.37 | multiple |
| D | Copolymer + Poly(ECH) | 15 (21) | 9.4 — 362 | 4.0 — 166 | 9.6 — 241 |
| E | Poly(ECH) | 0 | — | — | — |
| F | Poly(ECH) | 0 | 439 | 240 | 283 |

As apparent from Examples 6 through 8, molecular weights (Mw) of homo- and copolymers of (5) are generally in the range of 1,000–10,000.

While in accordance with the Patent Statutes, the best mode and preferred embodiment has been set forth, the scope of the invention is not limited thereto, but rather by the scope of the attached claims.

What is claimed is:

1. A process for the preparation of 4,4,4-trifluoro-2-methyl-1-butene from 3-chloro-1,1,1-trifluoro-3-methylbutane comprising the steps of:

heating the 3-chloro-1,1,1-trifluoro-3-methylbutane to an elevated temperature of at least about 100° C. in the presence of an effective amount of a base of an oxide or hydroxyl derivative of Group IA or 2A metal, or a sterically hindered alkyl-substituted pyridine wherein said alkyl group has from 1 to 7 carbon atoms, to selectively dehydrochlorinate said 3-chloro-1,1,1-trifluoro-3-methylbutane and yield 4,4,4-trichloro-2-methyl-1-butene.

2. A process according to claim 1, wherein said selective dehydrochlorination temperature is from about 100° C. to about 300° C.

3. A process according to claim 2, wherein said alkyl substituent of said pyridine is a primary alkyl group, a secondary alkyl group, or a tertiary alkyl group.

4. A process according to claim 3, wherein said selective dehydrochlorination temperature is from about 150° to about 250° C., and wherein said base is BaO, MgO, CaO, Na$_2$O, NAOH, or combinations thereof.

5. A process according to claim 4, wherein said base is MgO.

6. A process according to claim 1, wherein 1,1,1-trifluoro-3-methyl-2-butene is also produced and the ratio of said 4,4,4-trichloro-2-methyl-1-butene to said 1,1,1-trifluoro-3-methyl-2-butene is at least 1.0.

7. A process according to claim 5, wherein 1,1,1-trifluoro-3-methyl-2-butene is also produced and the ratio of said 4,4,4-trichloro-2-methyl-1-butene to said 1,1,1-trifluoro-3-methyl-2-butene is at least 500.

8. A composition of matter, comprising: a compound having the formula

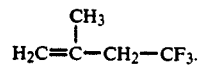

* * * * *